(12) United States Patent
Kim

(10) Patent No.: US 8,142,624 B2
(45) Date of Patent: *Mar. 27, 2012

(54) PORTABLE CONTACT LENS CLEANSING APPARATUS AND CLEANING METHOD OF CONTACT LENS

(76) Inventor: Chil-Young Kim, Gyeonggi-do (KR)

(*) Notice: Subject to any disclaimer, the term of this patent is extended or adjusted under 35 U.S.C. 154(b) by 1189 days.

This patent is subject to a terminal disclaimer.

(21) Appl. No.: 11/919,150

(22) PCT Filed: Apr. 25, 2006

(86) PCT No.: PCT/KR2006/001559
§ 371 (c)(1),
(2), (4) Date: Oct. 24, 2007

(87) PCT Pub. No.: WO2006/115369
PCT Pub. Date: Nov. 2, 2006

(65) Prior Publication Data
US 2009/0308758 A1    Dec. 17, 2009

(30) Foreign Application Priority Data
Apr. 26, 2005 (KR) .................. 10-2005-0034698
May 12, 2005 (KR) .................. 10-2005-0039891

(51) Int. Cl.
*C25B 9/06* (2006.01)
*C25B 1/13* (2006.01)
*C25B 1/30* (2006.01)
*C02F 1/467* (2006.01)

(52) U.S. Cl. ........ 204/271; 205/466; 205/626; 205/701; 205/742; 205/769

(58) Field of Classification Search ............... 204/271, 204/273; 205/466, 626, 701, 742
See application file for complete search history.

(56) References Cited

U.S. PATENT DOCUMENTS

| | | | | |
|---|---|---|---|---|
| 4,014,766 A | * | 3/1977 | Watanabe et al. | 205/756 |
| 5,129,999 A | * | 7/1992 | Holland et al. | 205/701 |
| 5,246,552 A | | 9/1993 | Kamiya et al. | 204/131 |
| 5,283,053 A | | 2/1994 | Kamiya et al. | 422/300 |
| 5,674,537 A | | 10/1997 | Morrow | 424/613 |

(Continued)

FOREIGN PATENT DOCUMENTS

JP    63-254417    10/1988
(Continued)

OTHER PUBLICATIONS

A. Steinbrecher. "Electrolytic production of hydrogen gas." Oil & Soap. Feb. 1939. pp. 36-39.*

Primary Examiner — Keith Hendricks
Assistant Examiner — Steven A. Friday
(74) Attorney, Agent, or Firm — Kusner & Jaffe

(57) ABSTRACT

The present invention provides a manufacturing method of normal saline solution and cleansing apparatus for contact lens, more particularly, a cleansing apparatus for contact lens comprising: a lens receiver for accommodating lenses, at least one electrode unit including a negative electrode and a positive electrode which set apart from the negative electrode each other, a power supply for supplying electric current to the negative electrode and the positive electrode, thereby effectively disinfecting and sterilizing viruses and bacteria and to remove foreign substances within the short time and protein on contact lenses in the lens receiver by oxidants generated by electrolysis in the electrode unit.

8 Claims, 15 Drawing Sheets

U.S. PATENT DOCUMENTS

| | | | |
|---|---|---|---|
| 6,261,464 B1 * | 7/2001 | Herrington et al. | 204/271 |
| 2002/0046957 A1 * | 4/2002 | Hough et al. | 205/744 |
| 2003/0062267 A1 * | 4/2003 | Nakamura et al. | 205/701 |
| 2003/0192780 A1 * | 10/2003 | Ala-Kleme et al. | 204/291 |

FOREIGN PATENT DOCUMENTS

| | | | |
|---|---|---|---|
| JP | 63254417 A * | 10/1988 | |
| JP | 08-327955 | 12/1996 | |
| JP | 11114036 A * | 4/1999 | |
| KR | 1989-0012180 | 8/1989 | |
| KR | 1993-0005434 | 8/1993 | |
| KR | 1998-0087837 | 12/1998 | |
| KR | 1999-0086756 | 12/1999 | |
| KR | 2000-0004303 | 3/2000 | |

* cited by examiner

PORTABLE CONTACT LENS CLEANSING APPARATUS AND CLEANING METHOD OF CONTACT LENS

FIELD OF THE INVENTION

The present invention relates to a manufacturing method of normal saline solution (hereinafter referred to as "NS") and cleansing apparatus for contact lens, more particularly, to such a manufacturing method and cleansing apparatus for contact lens with enhanced cleansing and disinfectant function whereby users or consumers personally can make and carry NS promptly and conveniently with the apparatus.

BACKGROUND OF THE INVENTION

In general, NS means achromatic and transparent salt solution having about 0.9 w/v % of the salinity, which is the same amount of osmotic pressure to man's body fluid and 4.5 to 8.0 of pH range. Especially, NS filtered and sterilized is used for washing rhinitis patients' noses and cleansing and sterilizing contact lens.

NS is manufactured as illustrated in FIG. 1. The manufacturing procedure is divided into sterilizing step S1 sterilizing a large amount of distilled water by heating water under approximate 121° C. with high pressure for about 30 minutes, a step S2 making saline water which has the same osmotic pressure to man's body fluid by put sodium chloride (NaCl) into sterilized distilled water as an osmotic pressure controller, a step S3 which put pH buffer agents to adjust acidity within pH 6.5 to 8.0, a step S4 which put antiseptic to limit the propagation of bacteria, a filtering step S5 to remove the impurities and a step S6 which pack the filtered normal saline solution in a container.

In the sterilizing step S1, the distilled water should be heated with high pressure and temperature.

In the step 2 S2, medicinal potassium chloride KCl can be used as an osmotic controller instead of medicinal sodium chloride and the salinity is adjusted to about 0.9 w/v %, the same salinity to man's body fluid.

The step 3 S3 is to adjust pH of NS to the range of man's body fluid by putting ph buffer agents such as boric acid, citrate, phosphoric acid.

The distilled water sterilized by high temperature and pressure keeps sterilized condition at the time of manufacturing, however, it can be deteriorated as time goes by. To prevent the propagation of bacteria, antiseptic such as solvate, dymed have been used.

Such conventional NS has been accomplished by sterilizing with high pressure and temperature. Unfortunately, with these procedures, a special container which can endure such high pressure and temperature should be required to sterilize NS and it can be only acquired by professional manufacturer so that general users or consumers cannot directly make and use NS because they do not afford to have the appropriate sterilizing apparatus under these conventional technology.

In other words, the professional manufacturer has manufactured a large amount of NS using a big container. Thus, manufactured with this procedure, NS has been packed in a relatively big size over 1 l in order to satisfy the consumer's convenience and the proper packing cost. However, NS packed in such a big package get easily contaminated after opening its package. In order to use fresh NS, user should use it up within 3~4 days after opening the package. In spite of the importance of uncontaminated condition of NS, users go on using it after passing 3~4 days without discarding the rest of NS. Therefore, it causes users to use contaminated NS. Furthermore, the antiseptic used to prevent the propagation of bacteria causes allergies for several users.

For these reasons, needs for using fresh NS have been increased.

On the other hand, contact lenses which directly contact with eyes are easily contaminated by residues from eyes and foreign substances from outside, and clean washing of the lenses is the important way to prevent the contamination. Therefore, these needs for making contact lenses clean by washing them well lead many studies on the effective cleansing method of contact lenses.

"Contact lens cleansing and sterilizing apparatus" Korea patent application No. 279,074 conceived by Lim, Sung Muk offered cleansing and sterilization of contact lenses in a cleansing apparatus with NS using ultrasonic wave generated by a vibrator and ultraviolet lamp. However, sterilization using ultraviolet wave by electrical vibration causes damage to contact lenses of hard type, and therefore, its use is limited to contact lenses of soft type.

Also, the sterilization using ultraviolet wave is not enough to remove bacteria and viruses attached on the surface of contact lenses or living in a normal saline solution.

Thus, the needs for easily portable contact lenses washer with excellent cleansing and sterilizing power which can be used regardless of a contact lens type and remove bacteria and viruses are increasing.

DETAILED DESCRIPTION OF THE INVENTION

Objects of the Invention

These disadvantages of the prior art are overcome by the present invention. It is an object of the present invention to provide a normal saline solution and manufacturing method to enable consumers directly and simply make and use NS.

Another object of the present invention is to prevent the use of antiseptics needed for keeping NS for a long time and to remove various problems in advance caused by the use of contaminated NS through the use of fresh NS made on the spot.

Still another object of the present invention is to provide a manufacturing method with effectively shorten NS manufacturing time through a self manufacturing method.

Yet another object of the present invention is to provide a cleansing apparatus for a contact lens sterilizing bacteria and virus as well as removing residues on the surface of a contact lens in a short time by forming oxidants with more acute electrolysis.

Still another object of the present invention is to provide a portable cleansing apparatus for contact lens of compact size which can be used everywhere users want to make NS by realizing the cleansing function with simple structure and, furthermore, cost reduction.

SUMMARY OF THE INVENTION

In order to attain the above mentioned object, the present invention provides manufacturing method of a normal saline solution comprising: a saline solution manufacturing step to put sodium chloride into water, a sterilizing the saline water through electrolysis and a filtering step removing impurities of the sterilized saline water.

The present invention simplifies the process of the conventional art, which needs a large-scale equipment for sterilization using high pressure and temperature, through electrolysis and sterilizing saline water with oxidants (ozone, hydro peroxide, HOCl, OH radicals etc.). Especially, in the case of electrolysis of saline water with 0.9 w/v % salinity, the electrolysis generates oxidants more promptly so that it shortens the manufacturing time of NS.

The sterilizing step is realized by oxidants $O_3, H_2O_2$, OH radicals, HOCl generated by electrolysis of saline water.

Herein, the oxidants are generated by supplying electric current with at least one positive electrode in the saline solution and at least one negative electrode in the saline solution apart therefrom each other, whereby electrolysis of the saline solution is caused. Hereinafter, the positive electrode and the negative electrode is to be referred to as "electrode unit". The oxidant formation and sterilizing process by electrolysis are attained by following (1) to (5) procedure.

(1) The process of ozone creation starts from electrolysis of $H_2O$ and finished with a combination of O and $O_2$.

$$H_2O \rightarrow H^+ + (OH)_{ads} + e^-$$

$$(OH)_{ads} \rightarrow (O)_{ads} + H^+ + e^-$$

$$2(OH)_{ads} \rightarrow O_2 + 2H^+ + 2e^-$$

$$*2(O)_{ads} \rightarrow O_2$$

$$(O)_{ads} + O_2 \rightarrow O_3$$

(2) $H_2O_2$ is made by a direct process of electrolysis of $O_2$ and indirect process of a combination of OH radicals, a medium generated by $O_3$.

That is,
direct course, $$O_2 + e^- \rightarrow O_2^-$$

$$O_2 + 2H^+ + 2e^- \rightarrow H_2O_2$$

Indirect course, $$OH\cdot + OH\cdot \rightarrow H_2O_2$$

(3) HOCl is formed by chemical reaction with $H_2O$ after combining with Cl⁻ existing in water with $Cl_2$.

$$2Cl^- \rightarrow Cl_2 + 2e^-$$

$$2H_2O + 2e^- \rightarrow H_2 + 2OH^-$$

$$Cl_2 + H_2O \rightarrow HOCl + H^+ + Cl^-$$

(4) OH radicals are created and vanished too soon to measure it directly, but in the case of ozone existing in water, OH radicals are finally created forming radical chain cycle with reacting with $HO_2^-$, conjugate base of $H_2O_2$, or OH⁻.

$$O_3 + OH \rightarrow \text{Radical Chain Reaction} \rightarrow OH\cdot$$

$$O_3 + HO_2^-{}_{(conjugate\ base\ of\ H_2O_2)} \rightarrow \text{Radical Chain Reaction} \rightarrow OH\cdot$$

(5) Microorganisms existing in water get removed or inactivated by the oxidants, the following microorganism is removed by electroadsorption and the following microorganics gets removed by direct electrolysis reacting with e⁻.

That is, regarding the microorganism, $$M(\text{Microorganism}) \rightarrow \text{Electrosorption} \rightarrow \text{Inactivation}$$

Also, $$M(\text{Microorganism}) + O_3 \rightarrow \text{Inactivation}$$

$$M + OH\cdot \rightarrow \text{Inactivation}$$

$$M + HOCl \rightarrow \text{Inactivation}$$

And, regarding microorganics, $$M(\text{Microorganics}) + e^- \rightarrow M-$$

Also, $$M(\text{Microorganics}) + O_3 \rightarrow \text{Product}$$

$$M + OH\cdot \rightarrow \text{Product}$$

$$M + HOCl \rightarrow \text{Product}$$

That is, during electrolysis, oxidation or sterilization is performed by the various oxidants ($O_3$, $H_2O_2$, HOCl, OH radical) formed in the (1) to (5) procedures and, after the electrolysis, the sterilizing process can last due to the high residency characteristics of HOCl.

On the positive electrode and the negative electrode, projections having an acute end like cone which face each other are formed, and more electric charges are concentrated in the projections so that electrolysis is more prompted.

On the other hand, before the sterilizing step, a filtering step to remove impurities in the saline water can be included. This can effectively prevent the electrode unit from being contaminated by impurities attached to the electrode.

The water includes tap water or underground water as well as distilled water. Therefore, users can easily and promptly make NS using tap water or underground water. In case of using distilled water or purified water, a filtering step can be omitted.

In case of manufacturing a small amount of normal saline solution less than 1 l, the saline solution manufacturing step is realized by pouring into a container and pouring the appropriate amount of saturated saline solution is poured into the container and then mixing it to be approximate 0.9 w/v % of salinity. It is also possible to make saline water using medicinal sodium chloride directly. However, it is convenient, easier for measuring exactly to use saturated sodium chloride solution than to use sodium chloride directly. Also, the solubility of sodium chloride saturated solution according to the change of temperature almost does not change as shown in the following table 1. That is, as the quantity of salt soluble in water does not vary not too much with the temperature, it is more convenient to add saturated sodium chloride solution into the water in a container for making isotonic saline water to be used as normal saline solution.

TABLE 1

| Temperature(° C.) | −15 | −10 | 0 | 20 | 40 | 60 | 80 | 100 | 140 | 180 |
|---|---|---|---|---|---|---|---|---|---|---|
| Solubility | 32.73 | 33.49 | 34.22 | 35.8 | 36 | 36.6 | 37.3 | 38.4 | 42.1 | 44.9 |

On the other hand, in the case of manufacture of a large amount of NS over than 1 L, medicinal salt of tablet type of approximate 1 g is used. That is, after manufacturing salt tablet of 0.5 g, two medicinal salt tablets are used for manufacture of 1~1.2 l NS and four medicinal salt tablets are used for manufacture of 2.0~2.3 l NS so that users can make suitable saline water.

The sterilizing step is performed by the oxidants generated by electrolysis of saline water wherein the positive electrode and negative electrode are posed apart therefrom and receive adequate electric current for predetermined time. In the positive electrode and negative electrode, positive projections and negative projections having a sharp end which face each other are formed. The electrolysis hereby can be prompted because electric charges converge more on sharp ends of the projections of negative and positive electrode(s). Therefore, only a relatively low amount of electricity is needed to be supplied for creating the predetermined amount of the oxidants, and thus, the small battery can be applied. Further, as plural current paths separated apart from one another are formed between the positive projections and the negative projections whereby $Cl_2$ gas is distributedly generated with small amount at the respective current path. Therefore, $Cl_2$ gas is easily reacted with water $H_2O$ by increasing the contact area between $Cl_2$ gas and water $H_2O$ as described by the chemical equation in (3), and thus the generated amount of HOCl is maximized even when only low current is applied to the electrode. Herein, it is preferable that the negative projections and the positive projections are made of or plated with Pt, Ti, graphite etc. which promote electrolysis most. It is efficient for improving the reaction life that the thickness of the plate layer of the negative projections and the positive projections are thicker than that of other parts.

On the other hand, the present invention provides contact lens washer comprising: a lens receiver for accommodating lenses, at least one electrode unit including a negative electrode and a positive electrode which set apart from the negative electrode each other, a power supply for supplying electric current to the negative electrode and the positive electrode.

This is to disinfect and sterilize viruses and bacteria and to remove foreign substances and protein on contact lenses in the lens receiver by oxidants generated by electrolysis in the electrode unit.

Herein, the negative projections and positive projections confronting each other are formed in the negative electrode and the positive electrode respectively and more electric charges converge on the negative projections and the positive projections so that more vigorous electrolysis can be realized.

That is, when electric current is supplied with the negative projections and the positive projections which posed apart each other, water between the negative projections and the positive projections is electrolyzed. Herein, oxidants such as $O_3$, $H_2O_2$, OH radicals, HOCl are formed and sterilize microbes, viruses and bacteria. Oxidant formation by electrolysis and sterilizing step are attained as the foregoing (1) to (5) procedures.

Here, $H_2O_2$ generated in the procedure of electrolysis can make free radicals, HO.+O. and these free radicals decompose proteins into peptide and amino acid with low molecular weight so that protein turns into water-soluble substance and converges on a double-bound area, and epoxide is formed. (For instance, C=C—R become C—C—R) More specifically, free radicals formed in $H_2O_2$ have high reactivity and attacks other organic molecules like protein for stability of itself hereby oxidization of $H_2O_2$ decomposes protein into amino acid, water-soluble substance and remove protein on the surface of contact lenses.

In this manner, cleansing contact lenses by oxidants generated by electrolysis makes hard type contact lens be cleaned, which cannot have been washed due to the possibility of damage of the hard type contact lens. Furthermore, as contact lens washer of the present invention can sterilize contact lenses with a very simple structure, the contact lens washer of the present invention can be manufactured as a very small device, and thus, can be modified as a portable contact lens washer.

Herein, the negative electrode and the positive electrode form a plate shape, on which projections shaped like a pillar or having its sharp end are formed respectively to face each other, so that more electric charges can be concentrated on the end of the projections, and thus, electrolysis can be more prompted. Also, in order to induct more electrolysis in the unit area, it is preferable that the negative electrode and the positive electrode form plural pairs of plates or rods.

On the other hand, a branch plate ramified from the surface of the plate-shaped negative electrode and the plate-shaped positive electrode projects, and a branch plate ramified from the negative electrode and a branch plate from the positive electrode are arranged facing each other one by one, and the negative projections and the positive projections are respectively formed in the facing branch plates whereby electrolysis area can be maximized in the minimum space. Furthermore, additional branch plate can be formed from the branch plate, and negative projections and positive projections is formed in the facing side of the other branch plates extended from a negative electrode and a positive electrode.

Herein, in order to induct more vigorous electrolysis near the negative projections and the positive projections, it is desirable that the negative projections and the positive projections are made of platinum or plated with platinum. Here, platinum can cover the whole electrode, but it is more efficient to thickly plate the area which negative projections and a positive projections than other parts.

Alternatively, grooves instead of the positive projections and the negative projections can attain the identical effect by causing electric charges to converge on the specific areas.

Also, if the negative projections and the positive projections are made of platinum and are formed as proper size, projections can be replaced by screw connection. On the other hand, in order for reduce the manufacturing cost, the negative projections and the positive projections can be plated with titanium or be made of titanium or carbon.

Also, an operation button can be formed in the front side of a case of the contact lens washer, where the case covers the lens receiver, the electrode unit, and the power supplier. Therefore, after users put contact lens into the lens receiver and just press the operation button, the contact lens washer turns on during the setting time, and vigorous electrolysis starts between the electrodes whereby oxidants generated by the electrolysis wash, disinfect and sterilize contact lenses in the lens receiver.

The contact lens washer in accordance with the present invention washes and sterilizes viruses and bacteria using oxidants from electrolysis in the electrode unit and additionally comprises a vibrator generating ultrasonic waves so that it can wash contact lenses more promptly.

Also, in order to effect sterilizing efficacy of oxidants generated by electrolysis for rhinitis' patients through spraying the sterilized water to inside of their nose, the present invention includes a spray which connects with water in the lens receiver sterilized by electrolysis for spraying sterilized water to outside thereof.

For users' convenience, it is more desirable to apply a battery which can be easily purchased in the market. Also, rechargeable battery is also applicable.

In order to discharge the heat of an electrode unit, at least one fin for discharging the heat is formed near the lens receiver of contact lenses or the electrode unit, and a blowing fan to blow out the heat transmitted to the fin can also be comprised.

Also, inside of the lens receiver, a circulation fan circulating the water in the lens receiver is formed so that it causes sterilized water near the electrode unit to circulate around lenses promptly. Here, it is more efficient for the fan to circulate only when electric power is turned on. This makes lens washing quick and keep inside of the lens receiver in an aseptic condition.

Also, the present invention comprises at least one electrode fixture to fix the each electrode. And the electrode fixture is formed as a slot via which electric current can be supplied. That is, the negative electrode plate and the positive electrode plate can be easily fixed to the slot just by inserting the plate into the slots whereby the electrode unit can be easily installed inside of the lens receiver and the electrode unit can be easily replaced.

On the other hand, the electric power supplier can reverse the direction of the electric current to be supplied to the electrode unit. That is, anode power is firstly sent to the electrode unit working as a positive electrode, and then, after a specific period, the cathode power is changed to sent to the second electrode unit working as a negative electrode, whereby it can prevent residues from adhering to the each electrode during electrolysis. The specific period can be set 1 to 10 times or 2 to 5 days in advance or by the user's needs.

Also, a salt receiver for saline solution package or for salt powder package or tablet is formed in the case so that users can simply make normal saline solution using the saline package or salt accommodated inside of the salt receiver whenever they want.

For opening and closing of the lens receiver, a lens cover is pivotally attached to the case. Here, a rubber packing is formed in the low side of the lens cover to seal up the lens receiver so that outside air cannot intrude into the lens receiver. Therefore, the contact lens keep the lenses sterilized and clean condition for a long time.

Also, a valve to selectively connect the lens receiver with the outside can be formed in the lens cover. It is to open the valve for discharging gas from the lens receiver to outside in the case of using the contact lens washer in accordance with the present invention. Further, in the case of finishing the washing and sterilizing process, the valve can prevent the water and lenses in the lens receiver from being contaminated with outside air.

One of tapped water, underground water and distilled water can be applied for the contact lens washer of the present invention and saline water can be used for more vigorous electrolysis induction. In the case of using saline water, NS in the market also can be used, but users can make NS directly pouring tapped water into the lens receiver and mixing saline solution with appropriate amount of high concentrated saline water. NS of approximate 0.9 w/v % salinity has advantages to minimize the damage of the minute hollows on the surface of contact lenses and to induct more vigorous electrolysis so that washing procedure is more prompted. Here, while NS in the market can cause allergy reaction due to the antiseptics in the NS, self-making NS does not have such a malfunction.

On the other hand, the present invention provides salt package. It is to make users carry small capsule or ample instead of NS for contact lens washer and wash their contact lenses whenever and wherever they want.

Herein, the proper amount of saline solution is packed in a capsule or ample considering salinity necessary for making saline water having 0.7 w/v % or 1.5 w/v % in the lens receiver, preferably 0.9 w/v % salinity. Therefore, users simply can make saline water having salinity of NS by just putting a capsule or an ample into the lens receiver for one time of the contact lens washing. Here, the saline solution can be used by saturated saline solution, but it is more desirable to use a saline solution having proper salinity considering the amount of water in the lens receiver because it would be possible to use the saturated saline solution for making the water in the lens receiver of 0.9 w/v % salinity.

On the other hand, NS of approximate 0.9 w/v % salinity can be manufactured by applying bigger size of container and mixing more amount of saturated saline solution, granular salt or saline solution.

THE ADVANTAGEOUS EFFECTS OF THE INVENTION

As explained above, the present invention provides manufacturing method for NS having a saline water manufacturing step which makes saline water by putting sodium chloride into the water, a filtering step which filters impurities of the saline water, a sterilizing step which sterilizes the saline water using electrolysis and another filtering step to remove impurities of the sterilized saline water. That is, just by comprising electrode unit for sterilization and filtration instead of using a pressure container to endure high temperature and pressure for sterilization under the conventional technology, users can simply directly make NS for their own whenever and wherever users go.

The present invention does not use antiseptics for maintaining the quality of NS for a long time different from the conventional technology so that people allergic to antiseptics can use NS manufactured in accordance with the present invention.

Also, the present invention provides manufacturing method for NS which can make NS within 2~3 minutes, and thus, if water for eating is prepared, NS can be supplied within very short time because created oxidants by electrolyzing saline water in an electrode unit having a negative projections and a positive projections can promptly sterilize the water.

Still, small size of battery can be applied because the present invention includes projections on the electrode unit for electrolysis and small capacity of electric power is required to create the enough oxidants for disinfecting and sterilizing the lenses.

Furthermore, NS sterilized as above can be used for medicinal use such as sterilization of a burnt flesh or contaminated body area by spraying the manufactured sterilized water based on the principle that existing HOCl in the sterilized water keeps the water sterilized for a time being even after electrolysis.

Also, the present invention provides contact lens washer, wherein lens receiver accommodates at least one negative electrode and at least one positive electrode posed apart from the negative electrode, a power supplier which supplies electric current to the negative electrode and the positive electrode and inducts electrolysis whereby created oxidants disinfects and sterilizes contact lenses in the lens receiver. Also, the present invention also provides a capsule (which refers to the container having any shape) to accommodate salt using therein.

Herein, the present invention provides contact lens washer using electrolysis which can sterilize viruses, fungus, bacteria by generating oxidants in a short time between a negative projections and a positive projections facing each other and protrudedly formed in the negative electrode and the positive electrode respectively.

The contact lens washer in accordance with the present invention enhances a user's convenience because a user can simply make NS of approximate 0.9 w/v % salinity mixing easily obtained water such as tapped water or underground water with saline solution.

Also, the contact lens washer in accordance with the present invention has an effect that sterilizes viruses on a contact lens.

The contact lens washer in accordance with the present invention is not limited to the washer method by a vibrator, but includes oxidants generated from electrolysis so that it can be used for hard type contact lens as well as soft type contact lens.

Also, the contact lens washer in accordance with the present invention has a simple structure so that it can be small and portable and accordingly has a cost reduction effect.

Comprised of a spray which sprays the sterilized water by electrolysis in an electrode unit, the contact lens washer in accordance with the present invention can be used for rhinitis' patients for washing their nose.

A negative projections and a positive projections in the electrode unit make electric charges to converge and be concentrated on each electrode projections so that, even if the small amount of electric power is supplied to the electrode, adequate sterilization effect can be obtained.

On the other hand, the present invention provides a salt capsule containing saline solution and, therefore, users just need to carry small capsule or ample to use the contact lens washer instead of carrying heavy NS.

Embodiments

BRIEF DESCRIPTION OF THE DRAWINGS

Accordingly, the present invention will be understood best through consideration of, and reference to, the following Figures, viewed in conjunction with the Detailed Description of the Preferred Embodiment referring thereto, in which like reference numbers throughout the various Figures designate like structure and in which.

DETAILED DESCRIPTION OF PREFERRED EMBODIMENTS

The foregoing and other objects, features, aspects and advantages of the present invention will become more apparent from the following detailed description of the present invention when taken in conjunction with the accompanying drawings.

In describing the present invention, detailed description of laid-out function or structure is omitted in order to clarify the gist of the present invention.

Figure 2:
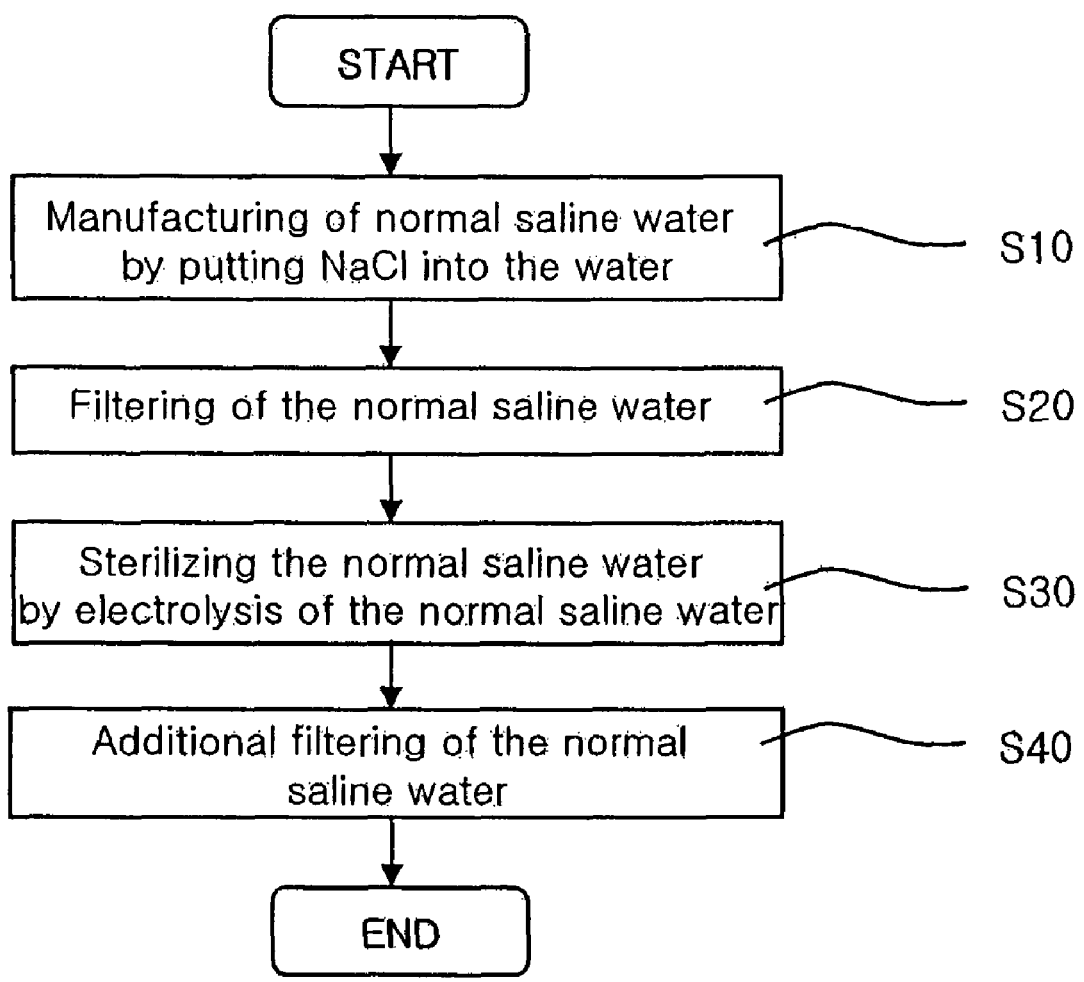
FIG. 2 is a diagram illustrating manufacturing process of the present invention in accordance with one embodiment.

Illustrated in FIG. 2, the manufacturing process of NS of the present invention in accordance with one embodiment includes a saline water manufacturing step S10 mixing tapped water with sodium chloride, a filtering step S20 to filter saline water for the first time and to remove impurities in the saline water manufactured in S10, a sterilizing step S30 sterilizing the filtered saline water by electrolysis and another filtering step S40 to filter the sterilized saline water and to remove impurities.

In the saline water manufacturing step, 1.8 g of sodium chloride is put into 200 ml of tapped water into a container for manufacturing saline water of 0.9 w/v % salinity. Here, because users usually do not have a scale for measuring the amount of sodium chloride, sodium chloride solution of proper salinity can be attained by adding 5.0 ml of saturated sodium chloride solution containing 0.8 g of sodium chloride considering that solubility of sodium chloride is 35.8. The amount of such saturated sodium chloride solution can be measured by reading a mark on a measuring container of small caliber so that user can simply make saline water.

The filtering step S20 is to prevent elctrode from being contaminated by impurities before sterilizing step S30.

Figure 3:
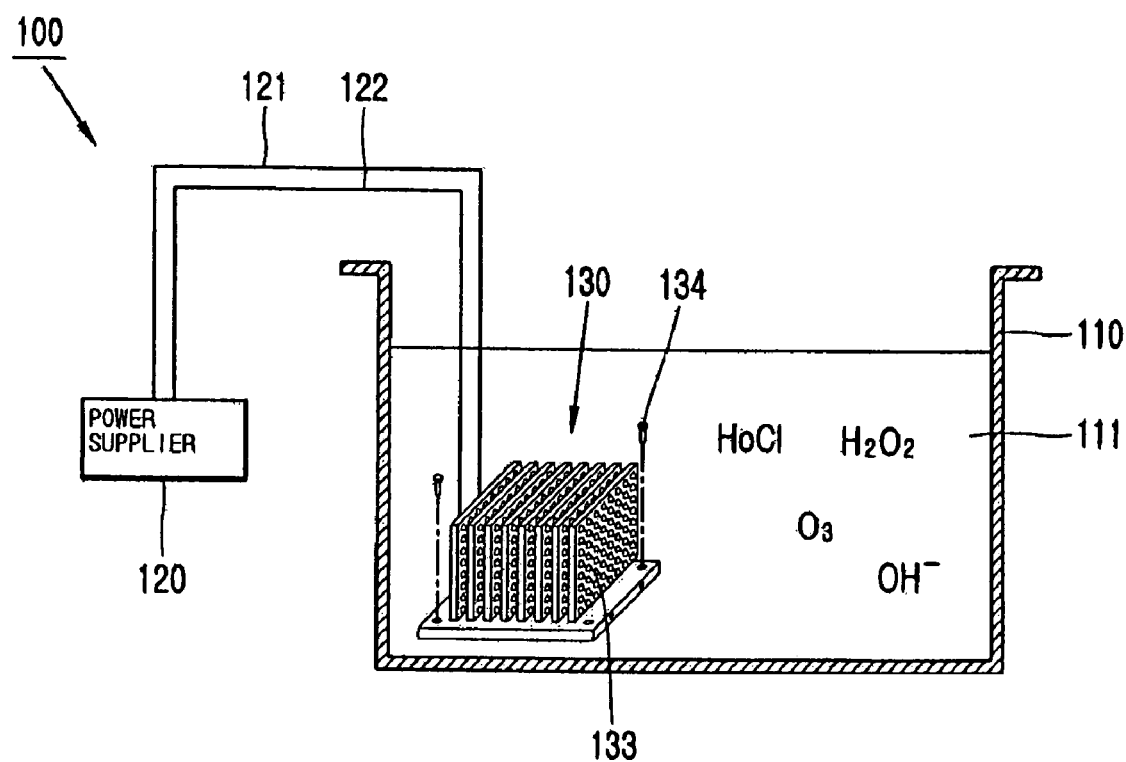
FIG. 3 is a diagrammatic representation of a structure of manufacturing apparatus in accordance with FIG. 2.

The sterilizing step S30 is attained by sterilizing apparatus 100 illustrated in FIG. 3. The sterilizing apparatus 100 comprises a container 110 for accommodating tap water 111, electric power supplier 120 and electrode 130 for electrolyzing the tap water receiving electric current from the power supply line 121, 122 from the electric power supplier 120.

Figure 4:
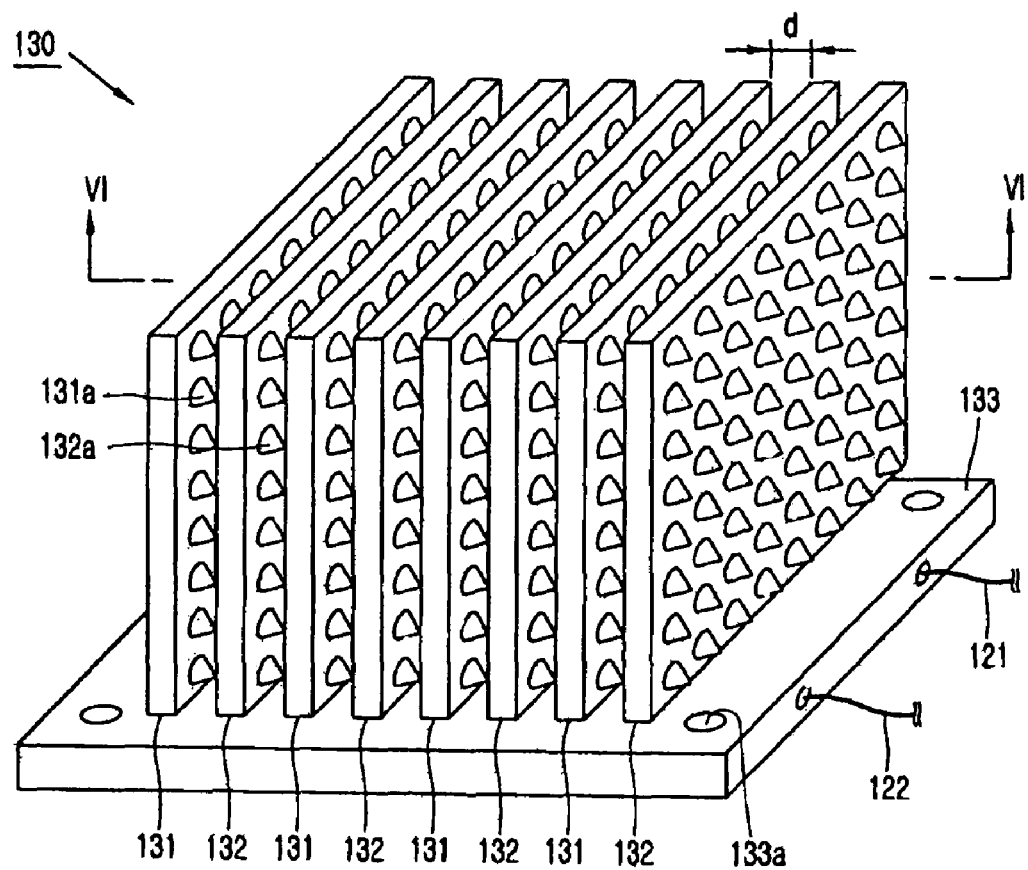
FIG. 4 is a perspective view illustrating a structure of an electrode unit.
Figure 6:
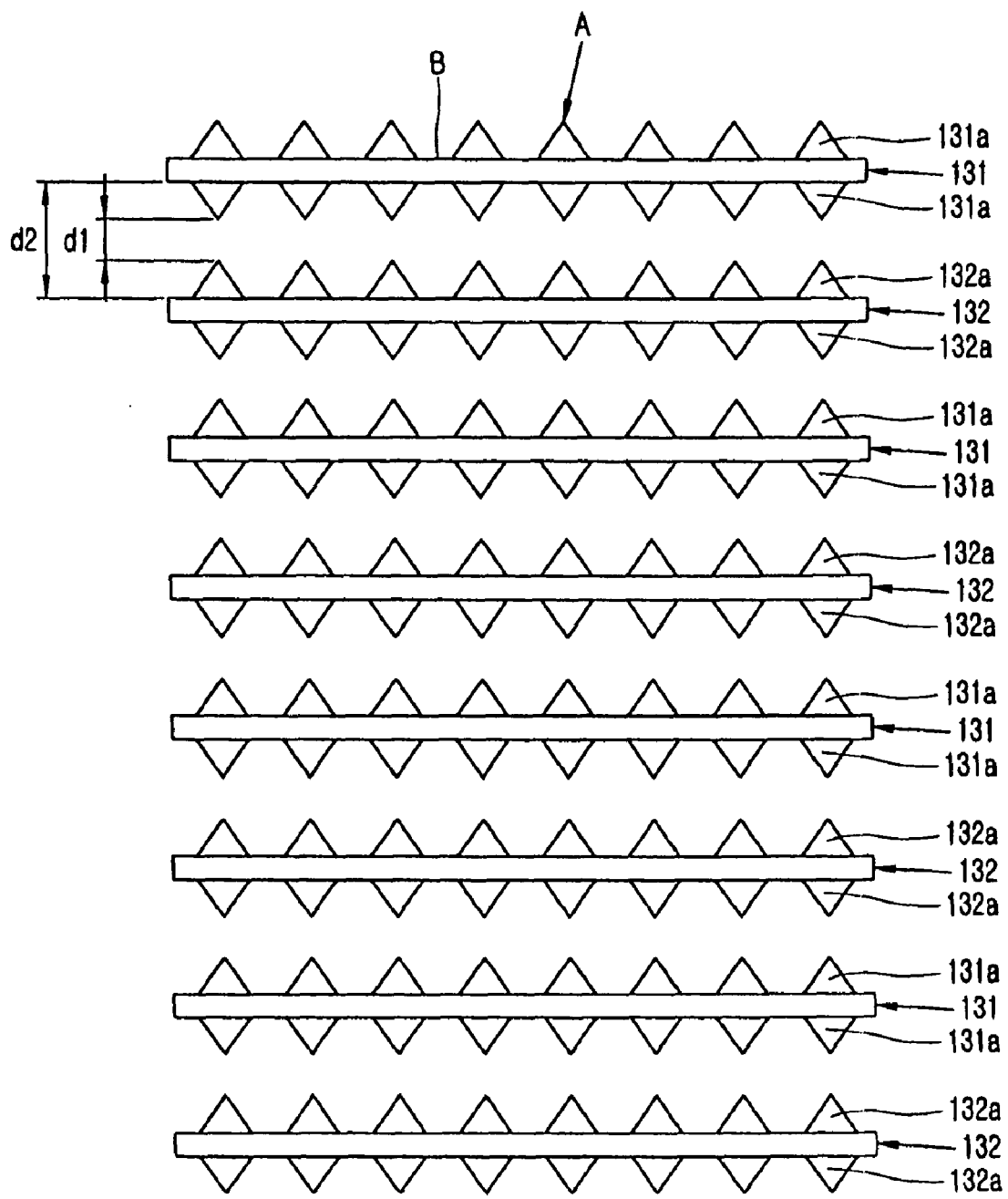
FIG. 6 is a cross sectional view by cut line VI-VI in FIG. 4.
Figure 8:
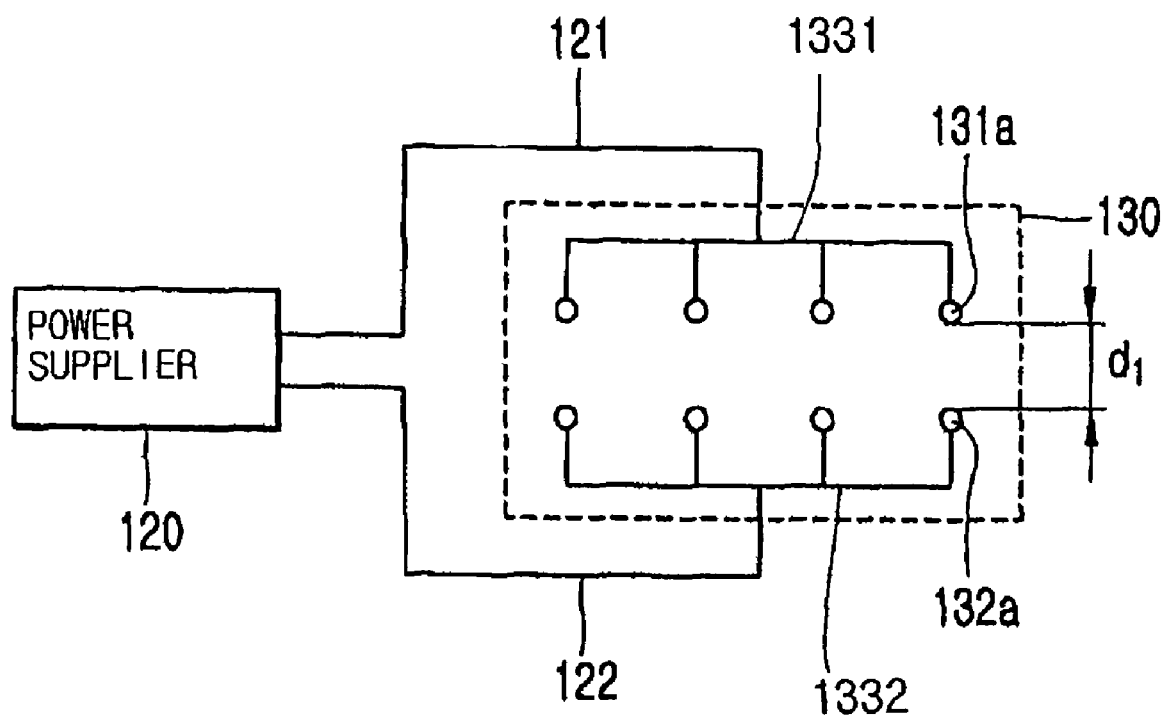
FIG. 8 is a wiring diagram illustrating power supply to an electrode of FIG. 3.

As illustrated in FIG. 4 or 8, herein, electrode 130 comprises several negative electrode plates 131 connecting with the electric power supplier 120 to transmit the negative electric current, several positive electrode plates 132 connecting with the supplier 120 to transmit positive electric current and a support 133 to install these electrode plates 131, 132 by inserting the end of the plates 132, 133. As illustrated in FIG. 6, a plurality of negative projections 131a and positive projections 132a shaped like a sharp cone and fully plated with platinum are formed at a distance d1 from each other on the electrode plates 131 and positive electrode plates facing each other.

When comprised as above, the sterilizing apparatus 100 attain to sterilizing step S20 to manufacture NS, the electric power is supplied to electrode plates 131, 132 from the electric power supplier 120 and then, electric charges are concentrated and converge in the negative electrode projections 131a and positive electrode projections 131b formed on each electrode plates 131, 132. Therefore, vigorous electrolysis of tap water between projections 131a and 131b is realized and oxidants like ozone, $H_2O_2$ and OH radicals etc. are generated by the electrolysis only for 2~3 minutes, which remove microbes in the tap water whereby NS with enhanced sterilizing effect can be manufactured.

More particularly, $O^-$ sterilizes viruses and bacteria with strong oxidization, $OH^-$ sterilizes and removes heavy metal as an alkali, $O_2$ makes water with high quality magnifying existing $O_2$ in the water and $O_3$ removes viruses, bacteria, fungus and spores with strong sterilizing power. Therefore, the NS manufactured as above can meet the permissible number of microbes for standard NS which should not include bacteria over than 100/g or 100/ml, coliform *bacillus, pseudomonas aeruginosa, staphylococcus aureus* and *Salmonella enteritidis*.

NS passing the additional filtering step S40 can more suitably fit to drinking water by filtering sterilized saline water and removing the impurities again.

NS manufactured by the above procedures can also meet the standards for NS within pH range of 4.5~8.0, and, without any special equipment, users can personally and simply make NS at home or in the hospital because of using electrolysis by supplying electric charges to the electrode plates having each negative and positive electrode projections.

Figure 11:
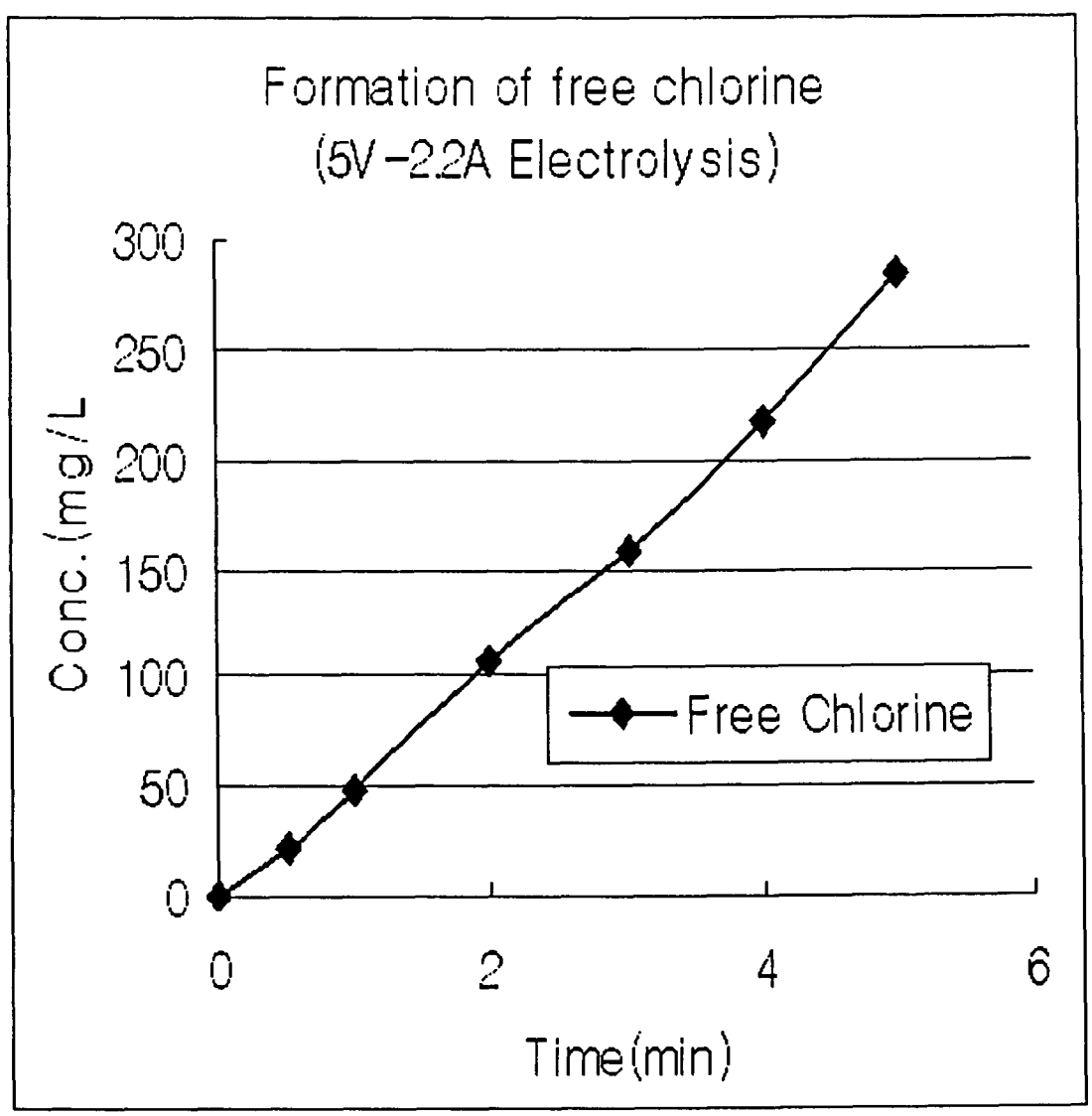
FIG. 11 is an experiment data graph illustrating measurement of chlorine ion increase in accordance with electrolysis of saline water.
Figure 12:
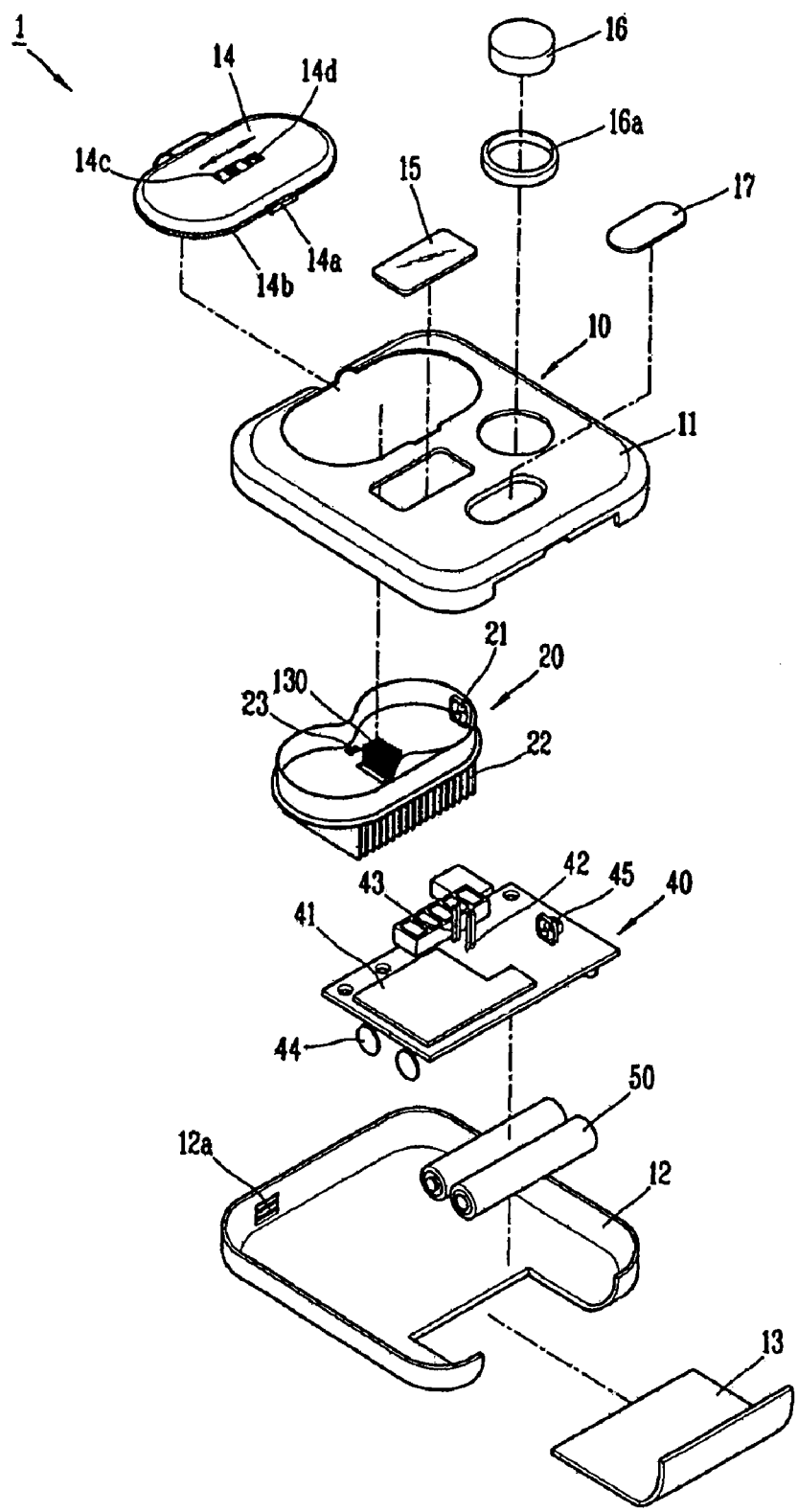
FIG. 12 is an exploded view illustrating the structure of the contact lens washer of the present invention in accordance with one embodiment.
Figure 13:
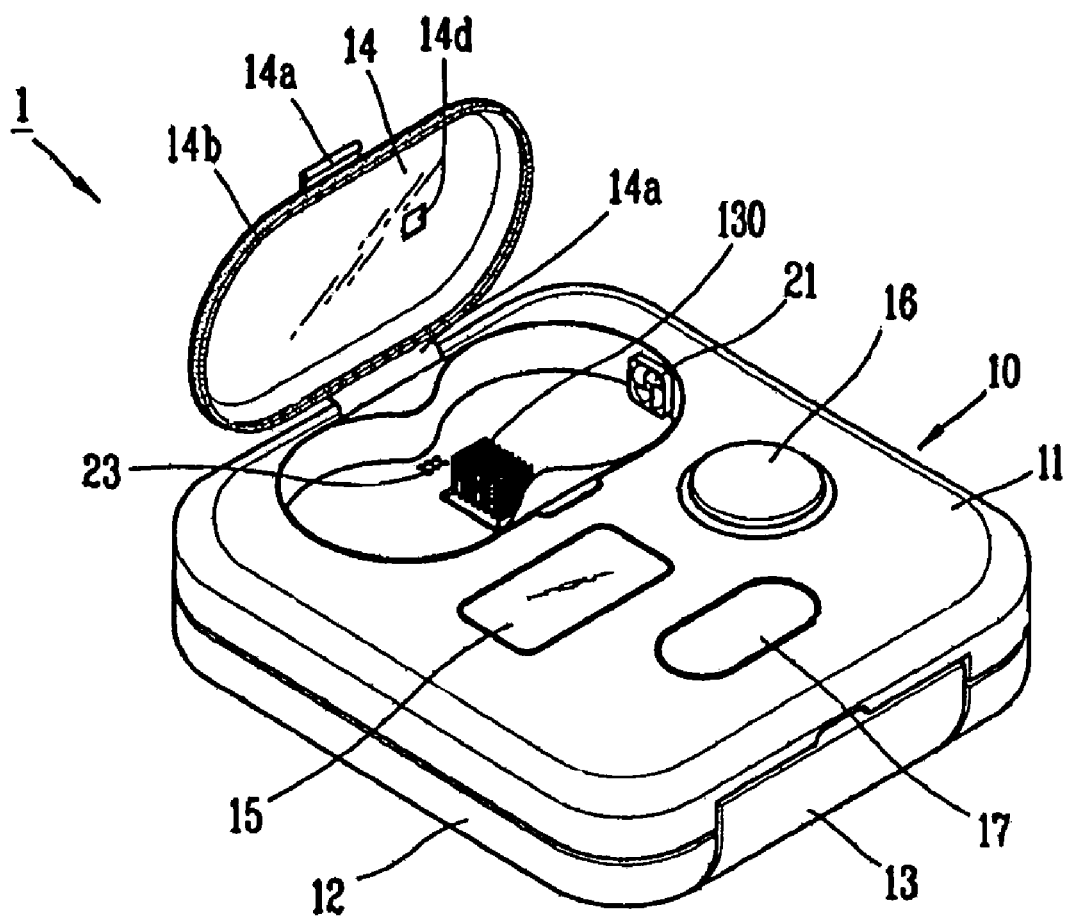
FIG. 13 is a perspective view illustrating the structure of the contact lens washer with the open lens cover of FIG. 12.
Figure 14:
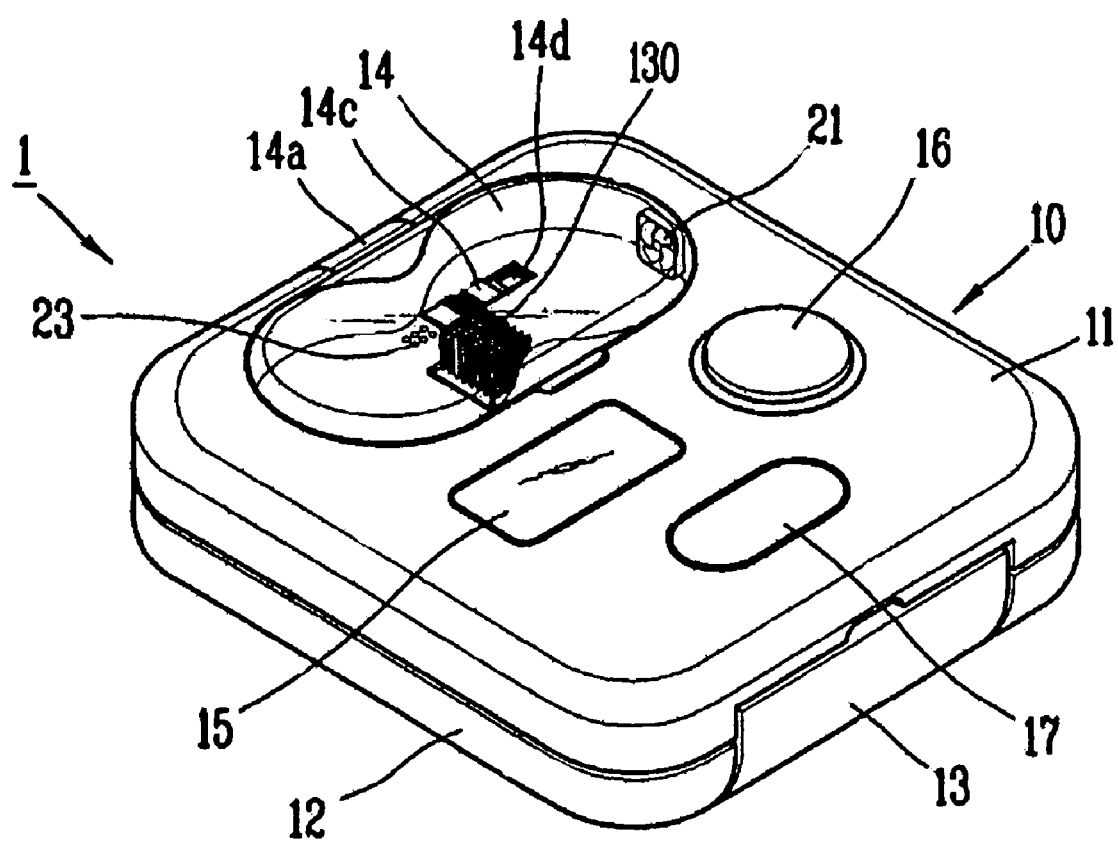
FIG. 14 is a perspective view illustrating the structure of the contact lens washer with the closed lens cover.
Figure 15:
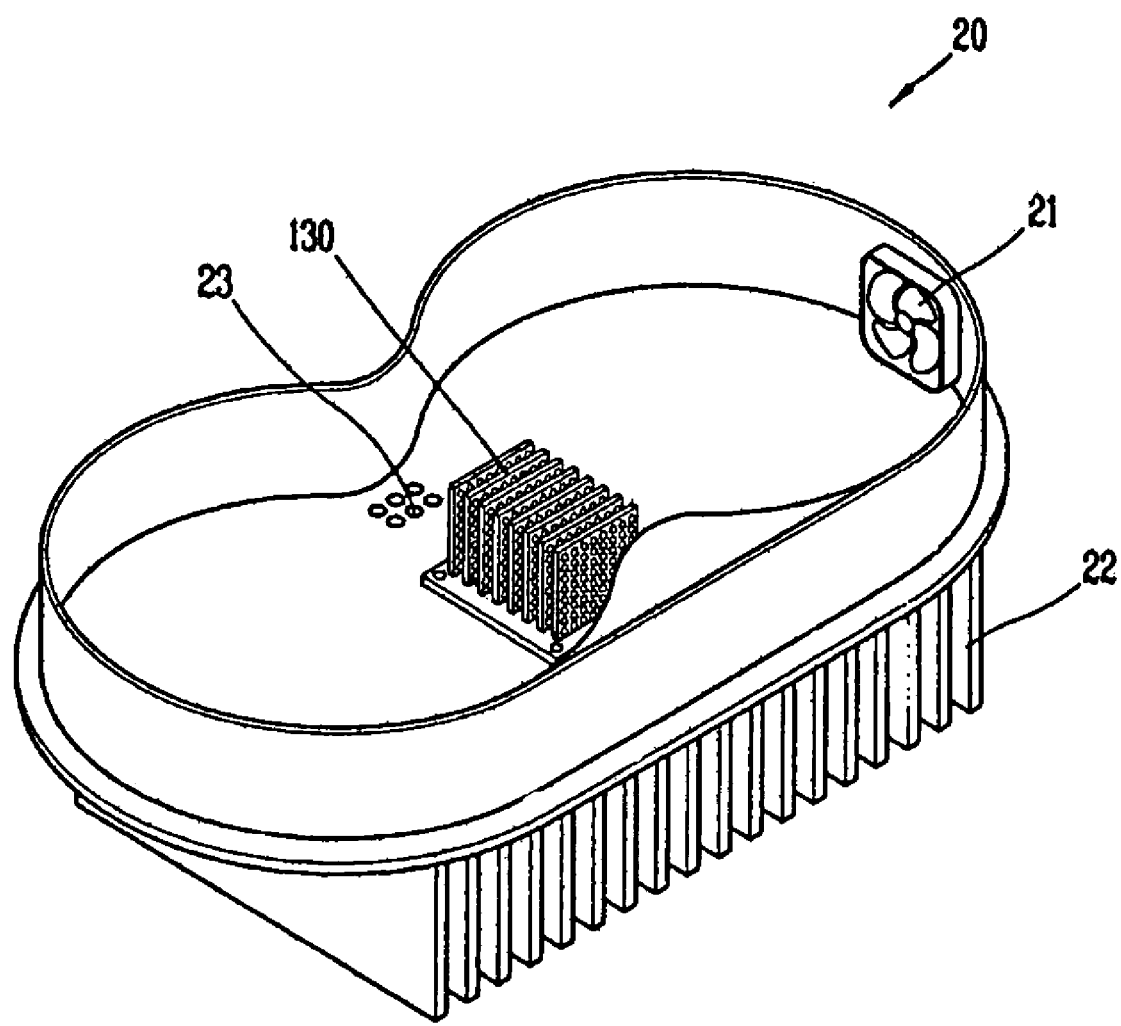
FIG. 15 is an enlarged view of a lens washer unit of FIG. 12.

On the other hand, electrolysis in saline water is more vigorous than that in the distilled water so that the generated number of oxidants is more increased in the saline water. FIG. 11 is an experiment data graph illustrating an increase of saline ion according to the electrolysis by supplying electric power of 5V, 2.2 A to the saline water having salinity 0.98 w/v % and pH 6.39. As shown in the experiment of FIG. 11, electrolysis is more vigorous in the saline water so that the sterilizing step S30 is more prompted. Furthermore, projections 131a, 132a to converge more electric charges are formed in electrode plates 131, 132 in accordance with one embodiment of the present invention whereby more vigorous electrolysis that FIG. 11 will be realized and the sterilizing time will be further shorten.

In one embodiment of the present invention, a saline water manufacturing step S10 includes a filtering step S20, a sterilizing step S30 and an additional filtering step in order, but, according to needs of a manufacturer belong to the technical field of the present invention, one more of the sterilizing step can be added or one of the filtering steps S20, S30 can be omitted.

FIG. 12 to FIG. 15 relates to the structure of a contact lens washer in accordance with one embodiment of the present invention. As shown in the Figures, a cleansing apparatus 1 for contact lens (i.e., contact lens washer 1) in accordance with one embodiment of the present invention comprises a case 10 covering outside, a lens receiver 20 installed within the case for receiving contact lenses, at least one electrode unit 30 generating oxidants by electrolysis when the DC electric power is supplied, a circuit board 40 for sending electric power to the electrode unit 30 and for installing other control unit, and a rechargeable battery 50 as a power source for supplying electric power to the circuit board 40.

The case 10 includes a front case 11 at which users look, a rear case 12 engaging with the front case 11, a battery cover 13 formed attachable to the rear case in order to detach the battery 50, a lens cover 14 pivotally connecting with the front case 11 in order to open or close the lens receiver 20, an indicator 15 showing the operation condition of the contact lens washer 1, an operation button 16 directing the operation by user's control and a cover 17 for a salt receiver formed concaved in order to carry saline solution capsule or granular salt capsule.

Herein, 'R' or 'L' (not shown) is marked on the lens cover 14 to distinguish right or left side of contact lenses. A locking projection 14a to prevent lens cover 14 from opening in the reverse condition, a rubber packing 14b formed in the low side of the lens cover 14 to prevent the lens receiver 20 from leaking, a valve 14c slided for the prevention of outside air intrusion in the closing condition and a hollow 14d which pass through the lens receiver 20 and outside according to the valve 14c movement are prepared. LCD marking the operation condition is formed inside of the indicator 15, and a ring 16a to assist the operation button 16 to attach to the front case 11 is inserted in the front case 11.

The lens receiver 20 is formed with a size available to receive left and right contact lenses and has a circulation fan 21 formed in one side for circulating the water inside of the lens receiver 20, a lots of fins 21 formed near the electrode unit 30 for emitting the heat generated from electrode 30 to the outside, a vibrator 23 for cleansing contact lenses with ultrasonic waves and a slot (not shown) to fit contact lenses inside of the lens receiver 20. Here, the vibrator 23 is selectively operating according to user's setting up.

The electrode unit 30, one of 130, 230, 430 in FIGS. 3 to 10 is fixedly installed horizontally or vertically, and detailed structure will be referred later.

The circuit board 40 includes a control unit 41 having an element operating by the electric power transmitted from the battery 50, an electric power supplier 42 connecting to the electrode unit 30 in order to supply electric power to the negative electrode plates 131 and the positive electrode plates 132 of the electrode unit 30, a second electric power supplier 43 supplying the power to the vibrator 23 with connecting to the vibrator and a battery terminal 44 transmitting the electric power of the battery 50 to the control unit 41.

Hereinafter, the operation principle of the contact lens washer in accordance with one embodiment of the present invention will be described.

Manufacturers calculate the best time for contact lens cleansing in advance and make the control unit 41 of the washer 1 memorized before delivering the washer in the market. After purchasing this contact lens washer, user opens the lens cover 14, put a right contact lens in the lens receiver marked 'R' and a left contact lens in the lens receiver marked 'L' and set up the valve 14c open.

Then, user pours somewhat clean water like tap water, distilled water or underground water into the lens receiver 20, open a capsule (not shown) with relatively high salinity to make NS of 0.9 w/v % salinity with the water and mix the capsule with the water in the lens receiver 20 whereby the water in the lens receiver 20 turn to be the same concentration of NS, i.e., about 0.9 w/v % salinity. On the other hands, NS purchased in the market can be used.

Then, User presses the operation button 16 for contact lens for cleansing and sterilizing the water and the lenses, then, negative electric power and positive electric power are respectively supplied to the negative electrode plates and the positive electrode plates inside of the lens receiver only for the set-up time. Here, 'now operating' message is shown in the indicator 15 to notice that electric power is supplied to the electrode unit. Here, in the case of the lens receiver not including the water, a positive electrode and a negative electrode posed apart from each other automatically stop the electric current' flowing because the electric current can be supplied through the water or saline water between positive electrode plates 131 and negative electrode plates 132.

For a set-up time, as electric power is sent, active electrolysis generates oxidant within a short time, and the circulation fan 21 inside of the lens receiver 20 circulate the water in the lens receiver 20. At the same time, in order to emit the heat generated from the electrode unit 30, the circulation fan 45 near to the fin 22 formed protruded near to the lens receiver 20 rotates and emit the hot outside of the lens receiver 20 through a ventilating opening 12a of the rear case 12.

After finishing the contact lens cleansing and sterilization by oxidants generated from the electrode unit for a set-up time, 'Finished' message is shown in the indicator 15. After the cleansing and sterilization finished, user can keep the lens receiver closed in order to prevent lenses from being contaminated by outside air if user wants to keep lenses for some times or some days without wearing those lenses. Therefore, the contact lens can keep sterilized and clean condition for a long time.

On the other hand, when user wants to clean the contact lenses again using the contact lens washer 1 after using it 1 to 10 times, the electric current supplied from the electric supplier 42 is reversed. Therefore, the negative electrode plates 131 and the positive electrode plates 132 can keep clean condition without residues attached by electrolysis.

Also, different recognizing the signal of pushing the operation button according to one time or two times makes differently control the time sending electric power to the electrode unit 30. That is, as the time for dissolving protein lasts rather longer than the time for general cleansing, user can control the time by pushing the operation button 16 two times according to user's needs for more perfect cleansing and sterilization. Here, the structure which electric power is supplied to only some parts (not all parts) of electrode unit 30 can realize the similar effect to the foregoing.

Figure 7:
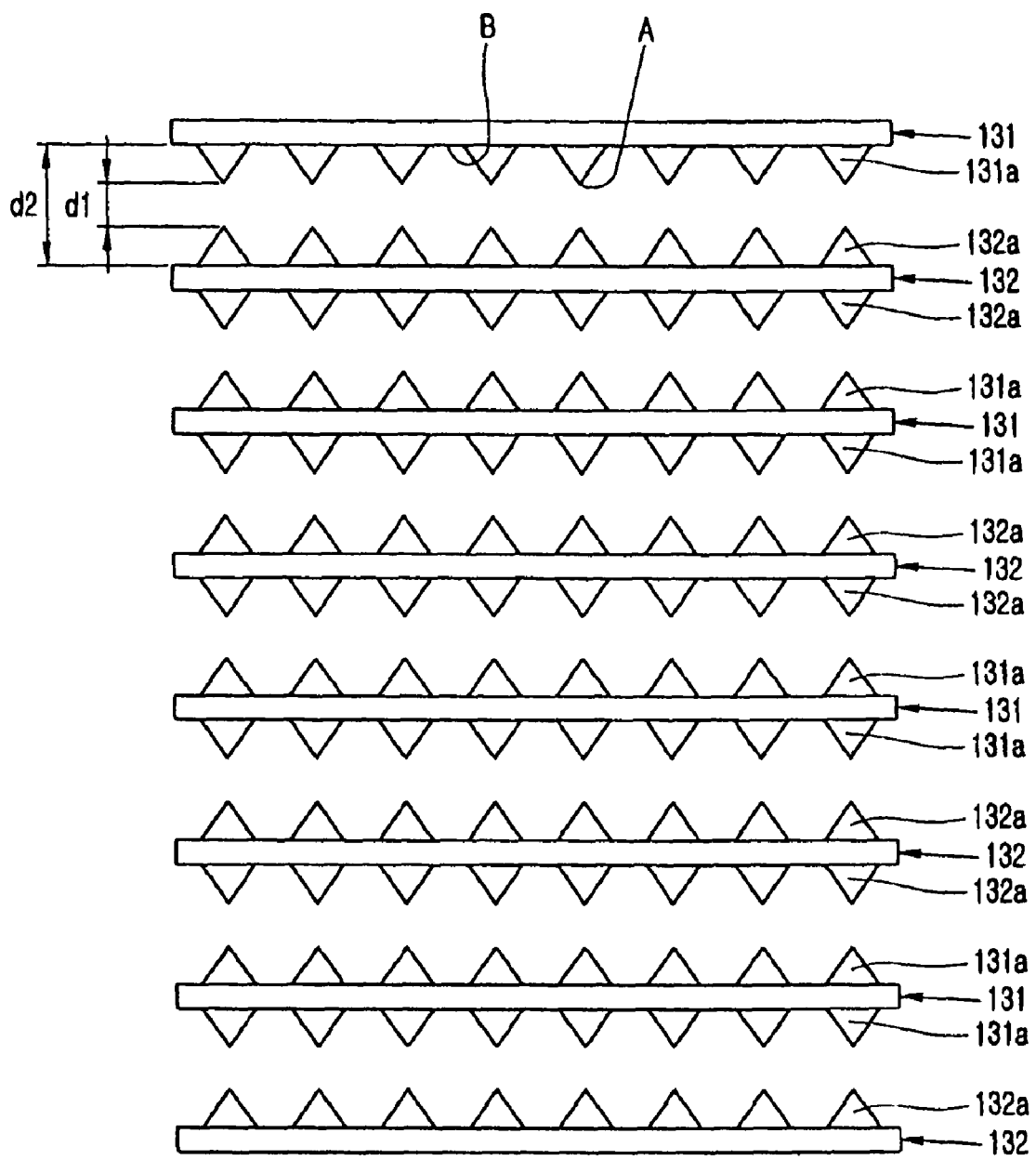
FIG. 7 is a cross sectional view of the electrode structure of another type.

In other words, as shown in FIGS. 6 and 7, the contact lens washer 1 in accordance with one embodiment of the present invention uses a principle which installs the positive electrode plates 131 and the negative electrode plates 132 apart therefrom about a distance d2 within the water 111 of the container 110, and, inducts electrolysis in the water by receiving the electric power through the electric power line 121 from an electric power supplier 120 and sterilizes bacteria and viruses using oxidants like ozone, OH radicals generated by the electrolysis. More particularly, the electrode unit 30 can be structured as one of electrodes 130, 230, 430 shown in FIGS. 4 to 10.

Figure 5:
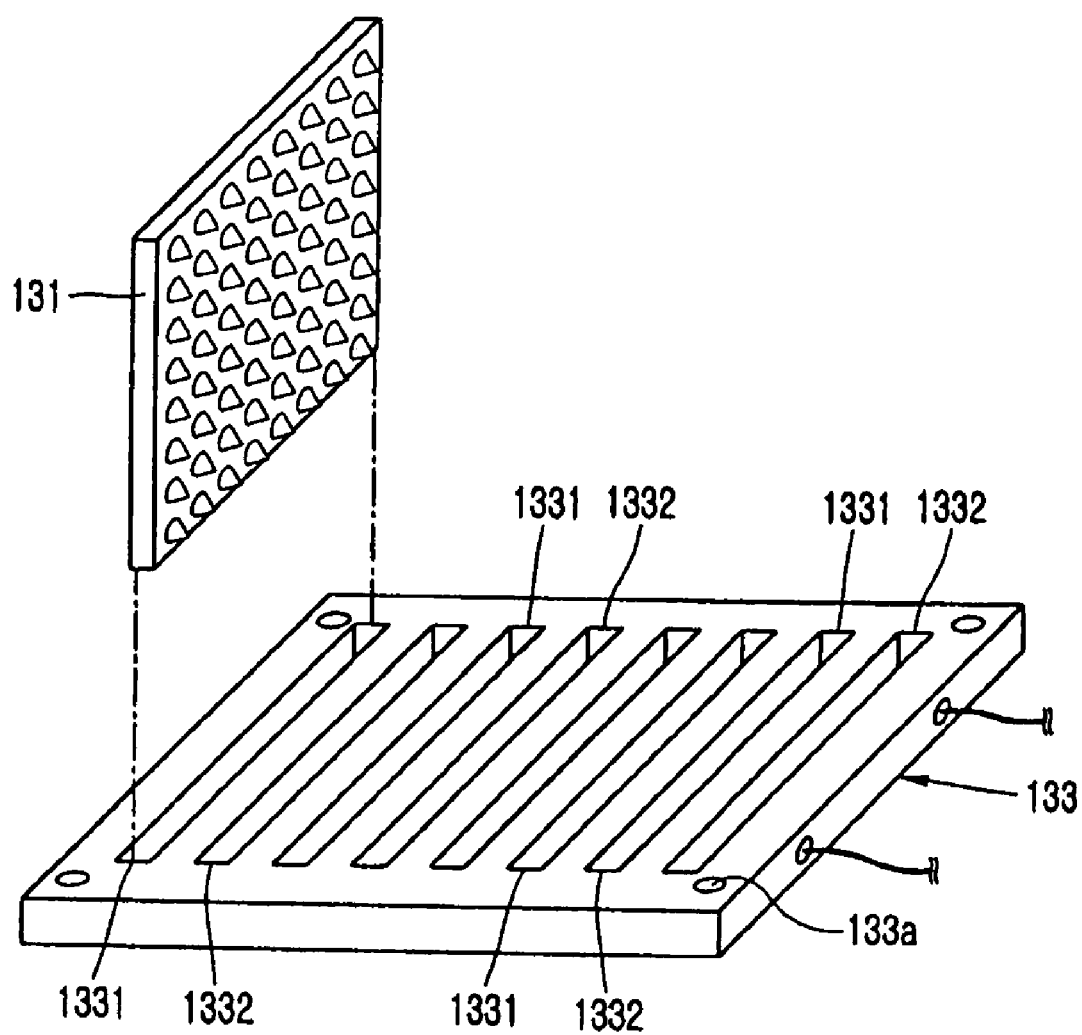
FIG. 5 is a separated perspective view of FIG. 4.

Herein, as illustrated in FIG. 5, the apparatus 100 having an electrode unit 130 comprises a container 110 for receiving the water 111, the electrode unit 130 fixed to the ground of the container 110 and an electric power supplier 120 supplying the electric power to the electrode unit 130.

The electric power supplier 120 can use AC power, DC power converted from AC and DC power supplied from a battery. A negative electrode line 121 from the electric power supplier is connected to negative electrode plates 131 and a positive electrode line 122 is connected to positive electrode plates 132.

The electrode unit 130 includes negative electrode plates 131 having a plurality of negative projections 131a on its surface, positive plates 132 having plurality of positive projections 132a and a support fixed to the ground of the container 110 fixing the negative electrode plates 131 and the positive electrode plates 132.

Herein, the negative electrode plates 131 and the positive electrode plates 132 are fixed to the support 132 at a distance d2 and have negative electrode projections 131a and positive electrode projections 132a projected and formed like a cone on sides B which face each other at a distance d1 whereby electric charges sent to the electrode plates 131, 132 converge on a fore-end B of projections 131a, 132a. Therefore, with the same amount of electric power, the negative electrode projections and the positive electrode projection make electrolysis of the water between them more acute.

Also, the negative electrode projections 131a and the positive electrode projections 132a are plated with more platinum than other parts so that the electrolysis can be more activated.

As illustrated in FIG. 5, the support 133 includes concave connection slots 1331 for fixing the negative electrode plates 131 and concave connection slots 1332 for fixing the positive electrode plates 132. As shown in FIG. 8, a negative electrode line 121 is connected to the connection slot 1331 of the negative electrode plates 131, and the positive electrode line 122 is connected to the connection slot of the positive electrode plates 132 inside of the support 133 so that simply inserting the support 133 into the slots 1331, 1332 can provide an environment of supplying electric power to the electrode plates 131, 132.

When the platinum of the electrode plates 131, 132 is used up, the electrode plates 131, 132 can be separated and new electrode plates 131, 132 are replaced and inserted into the respective slots 1331, 1332. Therefore, comprised as above, the contact lens apparatus 100 can be permanently used.

Hereinafter, the apparatus 100 having the electrode unit will be described.

When user wishes to clean, disinfect and sterilize contact lenses using the apparatus 100, user pours tap water 111 into a container 100 and sends electric power from the electric power supplier 120, then the electric power is supplied to a connection slots 1331 of negative electrode plates 131 and slots 1332 of a positive electrode plates. Then, negative electric power is supplied to the negative electrode plates 131 and positive electric power is supplied to the positive electrode plates 132 through each connection slots 1331, 1332. Here, electric power is sent to the negative electrode plates 131 and the positive electrode plates 132 respectively, and the electric charges converge on the negative electrode projections 131a and the positive electrode projections 132a facing each other in each electrode plates 131, 132. Therefore, the electrolysis between projections 131a, 132a generates oxidants like ozone, H2O2, HOCl, OH radicals actively so that it cleans, disinfects and sterilizes residues, protein, viruses and bacteria on the contact lenses in a short time.

The apparatus 100 needs only the electrode plates 131, 132 having projections 131a, 132a inside of the container so that it can be designed portable size. Here, a controller having a timer to induct electrolysis for a set-up time can be included.

Figure 9:
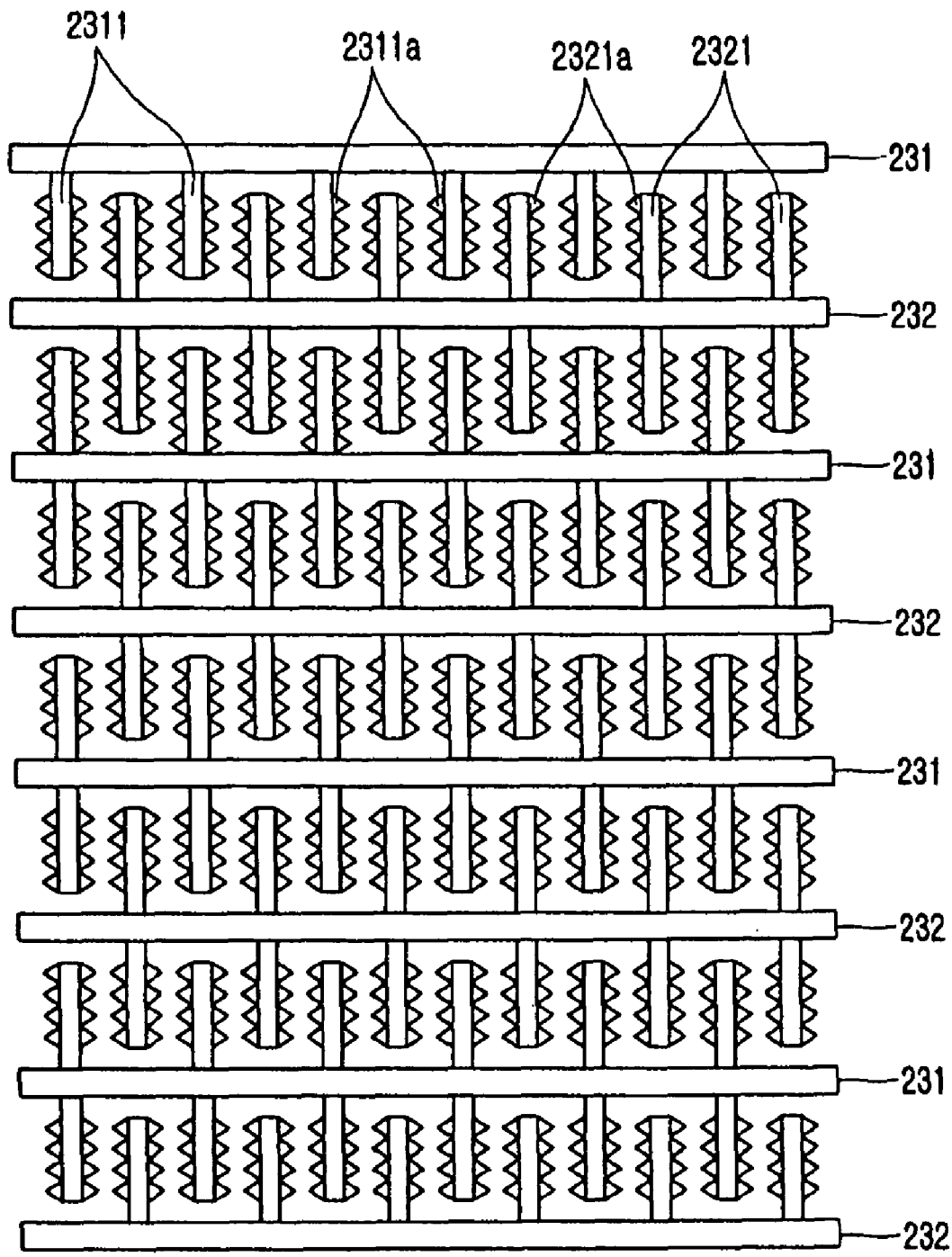
FIG. 9 is a cross sectional view of the electrode structure in accordance with another embodiment.

On the other hand, as shown in FIG. 9 as another shape of the sectional view of FIG. 4, electrode plates 231, 232 can include branch plates 2311, 2321 from electrode plates 231, 232, and further, the negative projections 2311a and the positive projections 2321a can be formed in the branch plates 2311, 2321 facing each other at a near distance than the electrode plates 231, 232.

The structure as above has an advantage of manufacturing sterilized water used for contact lenses cleaned, disinfected and sterilized for a short time based on the principle that the more area for electrolysis can be realized.

Figure 1:
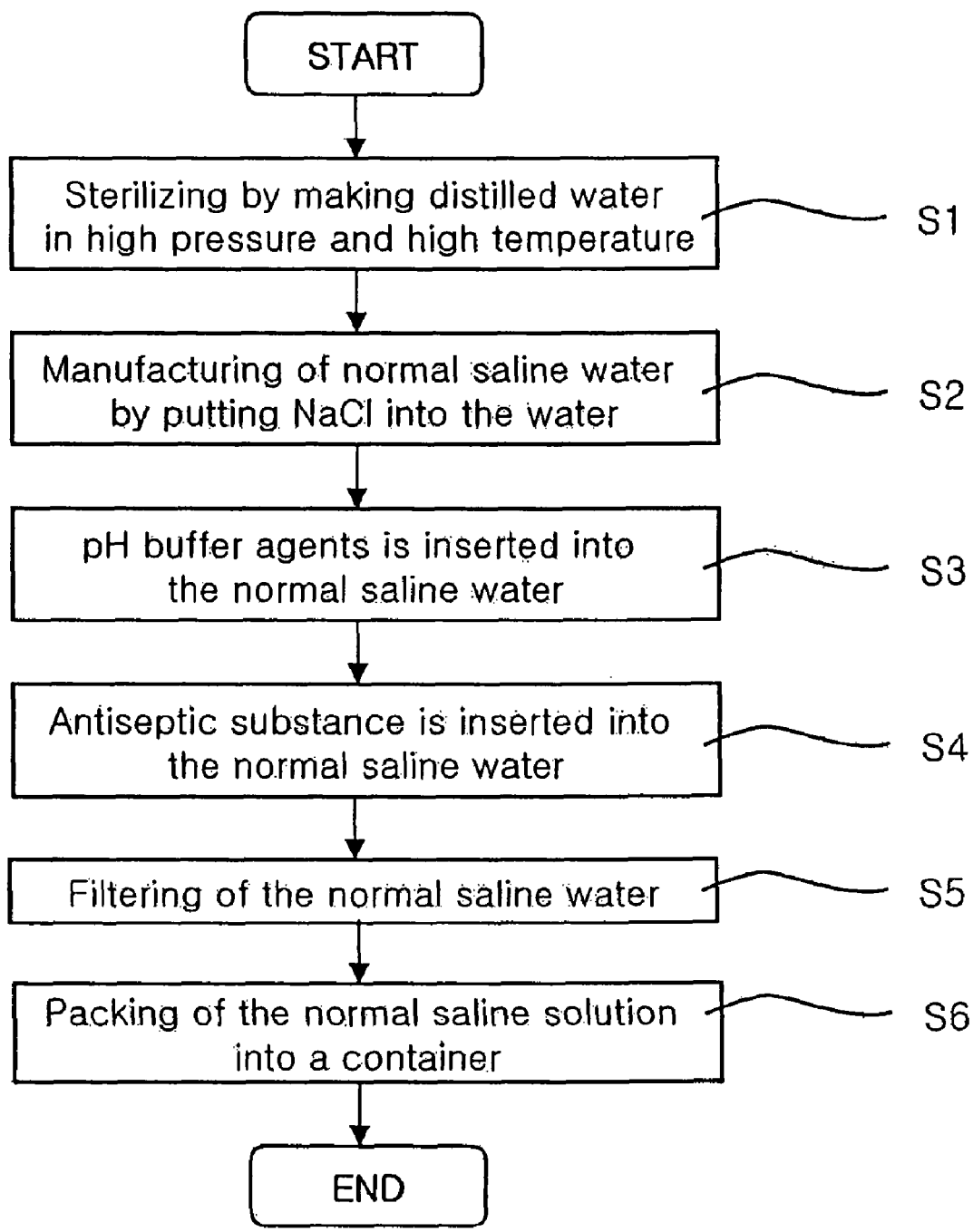
FIG. 1 is a diagram showing manufacturing process of the prior art.
Figure 10:
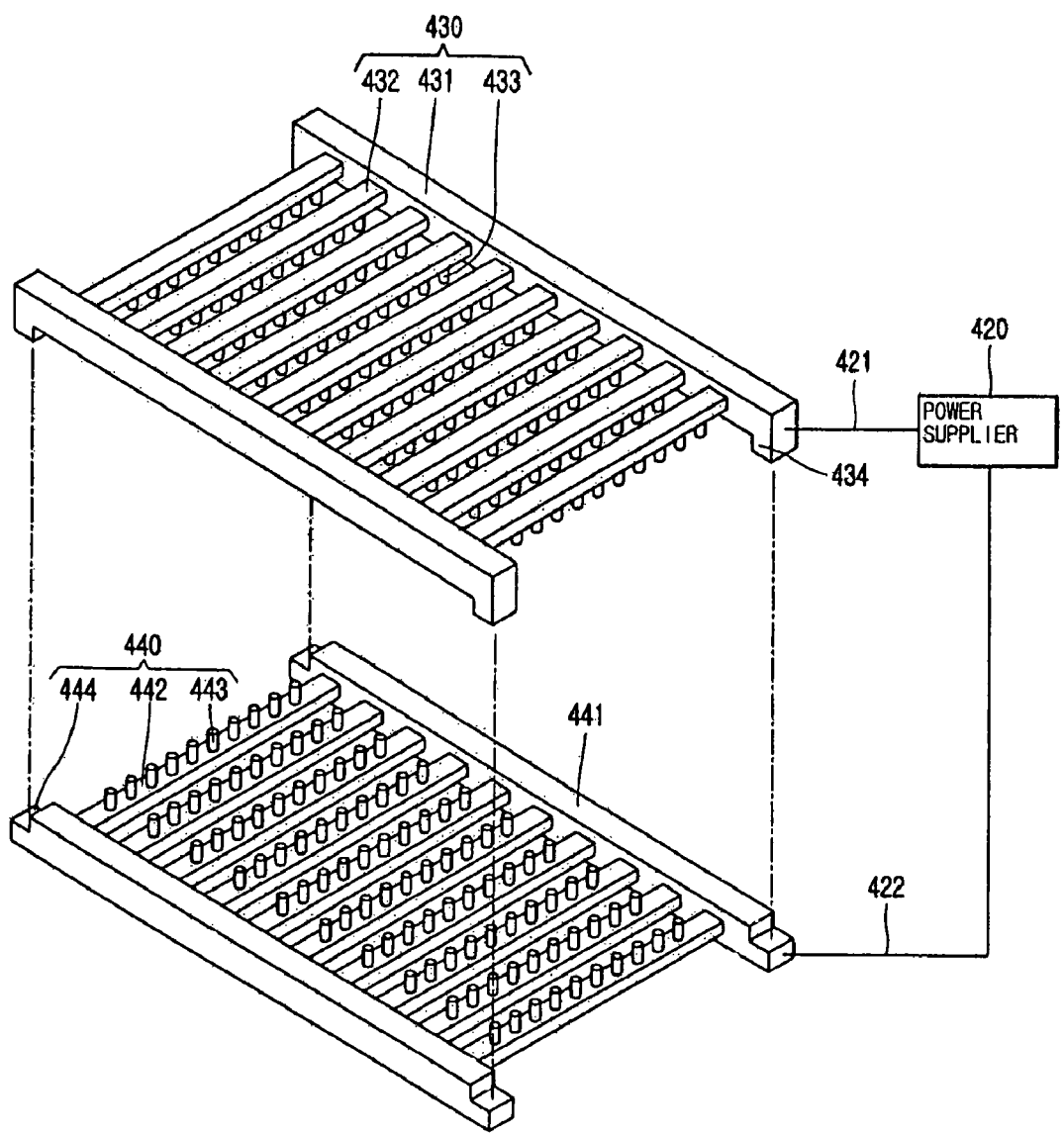
FIG. 10 is a cross sectional view illustrating the structure of electrode of FIG. 3 in accordance with another embodiment.

FIG. 10 is a sectional view illustrating another structure of the electrode unit in FIG. 1. Compared with the electrode unit 120 in FIG. 4, the electrode unit 430 in FIG. 10 has a feature that comprises a negative electrode unit 430 supplied negative electric power through a negative electric power line 421 from an power supplier 420 and a positive electrode unit 440 supplied positive electric power through a positive electric power line from the power supplier 420.

The negative electrode unit 430 includes two support rods 431 of negative electrode posed at a distance and connected to a negative power line 421, a negative electrode rod 432 which forms a plurality of rods between the support rod 431 of negative electrode, the negative projections 433 projected like a pillar on the low side of the negative electrode rod 432 to gather electric charges and a fitting projections 434 formed in the low side of the negative electrode support rod 431 to ensure a predetermined distance from the positive electrode 440.

The positive electrode unit 440 comprises two support rods 441 of positive electrode posed at a distance and connected to a positive power line 422, a positive electrode rod 442 which forms a plurality of rods between the support rod 441 of positive electrode, a positive projection 443 projected like a pillar on the upper side of the positive electrode rod 442 to gather electric charges and a fitting groove 444 formed in the upper side of the positive electrode support rod 441 to ensure a predetermined distance from the negative electrode 430.

Here, in order to prevent the electric current from flowing between the negative electrode 430 and the positive electrode 440, an insulator having a specific thickness is inserted between the fitting projections 434 and fitting groove 444 or coated for insulation. Also, in the condition of fitting the projections 434 to the groove 444, the fore-end of the negative electrode projections 433 keep a distances from the fore-end of the positive electrode projections 443 so that the vigorous electrolysis is inducted between them.

FIG. 11 is an experiment data graph illustrating the increase of saline ion according to electrolysis by sending electric power of 5V, 2.2 A to the saline water having salinity 0.98 w/v % and pH 6.39. As shown in the experiment of FIG. 11, electrolysis is more vigorous in the saline water so that the quick sterilizing effect can be achieved. Furthermore, projections 131*a*, 132*a* to converge more electric charges are formed in electrode plates 131, 132 whereby more vigorous electrolysis than the experiment in FIG. 6 will be realized and the sterilizing time will be much more shorten. Therefore, the water used for the present invention can include saline water as well as tap water, distilled water.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims. That is, exemplary embodiment of the present invention includes electrode projections shaped like a pillar in order to converge electric charges, but the shape is not limited to the pillar shape but should include any shape which can inducts the concentration of electric charges.

It is also clear that the shape of electrode unit is not limited to exemplary embodiment of the present invention, but should include any shape of electrode for inducting electrolysis.

The invention of claimed is:

1. A portable cleansing apparatus for contact lens comprising:
    a receiving unit accommodating at least one contact lens and salt solution made by mixing salt with one among tap water, underground water and distilled water;
    at least one electrode unit having a negative electrode within the receiving unit and a positive electrode within the receiving unit separated from the negative electrode and facing the negative electrode; and
    a battery for supplying direct current to the electrode unit, wherein the negative electrode has a plurality of negative electrode projections thereon, and the positive electrode has a plurality of corresponding positive electrode projections thereon, each positive electrode projection arranged to face and be aligned with each corresponding negative electrode projection.

2. The cleansing apparatus as claimed in claim 1, wherein a plurality of current paths are formed separately apart from one another between the negative electrode and the positive electrode.

3. The cleansing apparatus as claimed in claim 1, further comprising a button for applying the direct current to the electrode unit during a predetermined time.

4. The cleansing apparatus as claimed in claim 1, wherein the negative electrode projections and the positive electrode projections are formed as one of cones having an acute end or pillars.

5. The cleansing apparatus as claimed in claim 1, wherein the negative electrode projections and the positive electrode projections are formed by one of platinum, titanium or carbons.

6. The cleansing apparatus as claimed in claim 1, wherein the negative electrode projections and the positive electrode projections are plated by platinum or titanium.

7. The cleansing apparatus as claimed in claim 1, further comprising a salt receiver for accommodating at least one salt package of which amount is packaged to make the water in the receiving unit have a concentration of normal saline.

8. The cleansing apparatus as claimed in claim 1, wherein the salt solution is a solution of about 0.9 w/v % of salt.

* * * * *